United States Patent [19]

Kinnersley et al.

[11] Patent Number: 5,604,177
[45] Date of Patent: Feb. 18, 1997

[54] METHOD FOR STIMULATING PLANT GROWTH USING GABA AND SUCCINIC ACID

[75] Inventors: Alan Kinnersley, East Lansing; Robert Coleman; Edward Tolbert, both of Okemos, all of Mich.

[73] Assignee: Computational Systems, Inc., Knoxville, Tenn.

[21] Appl. No.: 500,391

[22] Filed: Jul. 10, 1995

Related U.S. Application Data

[63] Continuation of Ser. No. 200,218, Feb. 23, 1994, Pat. No. 5,439,873.
[51] Int. Cl.$^6$ .............................. A01N 37/44; A01N 37/04
[52] U.S. Cl. ........................ 504/147; 504/157; 504/158
[58] Field of Search ...................................... 504/147, 157, 504/158

[56] References Cited

U.S. PATENT DOCUMENTS

| | | | |
|---|---|---|---|
| 4,870,172 | 9/1989 | Okami et al. | 540/460 |
| 4,908,353 | 3/1990 | Yamamoto et al. | 514/19 |
| 4,950,606 | 8/1990 | Stirling et al. | 435/280 |

*Primary Examiner*—S. Mark Clardy
*Attorney, Agent, or Firm*—Luedeka, Neely & Graham, P.C.

[57] ABSTRACT

A process for increasing plant growth and productivity comprising treating the roots, stems and/or foliage of the plant with γ-aminobutyric acid and succinic acid as a readily metabolized source of carbon. The present invention also provides for a process for increasing plant growth and productivity comprising treating the roots of the plant with γ-aminobutyric acid and succinic acid, and a process for increasing the rate of root formation in a plant comprising treating the roots, stems and foliage of the plant with γ-aminobutyric acid and succinic acid. Further, plant growth is increased by application of mixtures of γ-aminobutyric acid and synthetic succinic acid, in a suitable carrier to a plant.

19 Claims, No Drawings

METHOD FOR STIMULATING PLANT GROWTH USING GABA AND SUCCINIC ACID

This application is a continuation of Ser. No. 08/20,218, filed Feb. 23, 1994, now U.S. Pat. No. 5,439,873.

FIELD OF THE INVENTION

The present invention relates to methods for stimulating plant growth by treating plants with organic compounds. In particular, the present invention relates to those methods which rely upon application of organic compounds including GABA to the plant's foliage, stems and/or roots.

BACKGROUND OF THE INVENTION

It is well known that organic acids are useful in stimulating the growth of plants. It has been theorized that much of the action of organic fertilizers, such as manure, is due to the presence of organic acids. These organic acids include those such as acids of the citric acid cycle or amino acids.

GABA (γ-aminobutyric acid), 4-aminobutyric acid, is an ubiquitous non-protein amino acid that is found in plants, bacteria and animals. Although the presence of GABA was discovered in plants more than forty years ago, its function remains unknown. As has been pointed out by Satya, Naryan and Nair (Review Article No. 51, *Phytochemistry* 29:367–375, 1990), the only known function of GABA is as an inhibitory neurotransmitter in animal nervous systems. Commenting on the possible functions of GABA in plants, Chung, et al., (*Plant Physiology* 99:659–664, 1992) have concluded that "such an abundant and ubiquitous compound will fulfill a significant physiological role". Thus, although an important role for GABA has been suggested, the nature of this role has remained a mystery.

SUMMARY OF THE INVENTION

In accordance with the present invention, it has now been discovered that GABA acts as a plant growth promoter and has other advantages when applied to growing plants. The present invention generally provides for a process for increasing plant growth and productivity comprising treating the roots, stems and/or foliage of the plant with γ-aminobutyric acid (GABA).

In a preferred embodiment of the present invention, the plant is further treated with a readily metabolized source of carbon along with the γ-aminobutyric acid (GABA). Preferred readily metabolized sources of carbon are selected from the group consisting of organic acids, amino acids, simple carbohydrates, and mixtures of organic acids, amino acids and simple carbohydrates. Preferred organic acids are selected from the group consisting of citric acid, malic acid, succinic acid, and fumaric acid; the amino acid is preferably glutamic acid; and the simple carbohydrates are preferably selected from the group consisting of sucrose and glucose. It is further preferred that the succinic acid is selected from the group consisting of synthetic succinic acid and fermention-derived succinic acid. A mixture of synthetic succinic acid and GABA is preferred over a mixture of fermention-derived succinic acid and GABA acid because, generally, it costs less and works better.

In another preferred embodiment of the process of the present invention, the roots, stems and foliage of the plant are treated with a solution having in the range of from about 2.5% to about 50% GABA and in the range of from about 97.5% to about 50% succinic acid with a suitable carrier medium. It is also preferred that the plant is treated with a solution having in the range of from about 1 ppm to about 5000 ppm γ-aminobutyric acid in a suitable carrier medium. Further, in one embodiment of the invention, the plant is grown hydroponically.

The present invention also provides for a process for increasing plant growth and productivity comprising treating the roots of the plant with GABA. In addition, the present invention also, provides a process for increasing the rate of root formation in a plant comprising treating the roots, stems and/or foliage of the plant with GABA.

DETAILED DESCRIPTION OF THE INVENTION

In the practice of the present invention, a solution of GABA, with or without other sources of carbon, is applied directly to the roots, stems and/or foliage of the plant. The application of the GABA to the plant stimulates growth and productivity such that increased yields may be seen with commercially important crop plants. Further, the application of the GABA increases the rate of root formation thus allowing the plants to better utilize the available nutrients in the soil.

Without being bound by theory, it is believed that GABA causes plants to grow if the plants are in a condition to grow. The presence of easily metabolized carbon compounds, such as organic acids on the citric acid cycle, amino acids, and/or simple carbohydrates, places plants in a condition to grow. Thus, although GABA works without the presence of those easily metabolized carbon sources, the presence of those sources synergizes the ability of GABA to increase plant growth.

As an example, GABA applied with succinic acid works better than the application of succinic acid, or GABA alone. It has also been noted that GABA works better in a mixture with pure succinic acid than in a mixture with fermention-derived succinic acid, such as disclosed in U.S. Pat. No. 5,143,833 to Dalta and U.S. Pat. No. 5,168,055 to Dalta, et al.

The solutions prepared according to the present invention may be advantageously applied to plants by any one of a number of means. Thus, the solutions may be applied by sprayer to roots, soil and/or foliage, for example.

The application of GABA to plant roots, stems and/or foliage has been found to be effective at concentrations of between about 1 ppm and about 5,000 ppm when mixed in a suitable carrier. Suitable carriers include distilled and tap water and fertilizer solutions. Such solutions as those prepared according to the present invention are, thus, relatively nonhazardous to the environment. The organic components added to the GABA solution are suitable sources of food for soil bacteria and thus will be readily broken down if not deposited on the plants.

In order to facilitate a further understanding of the invention, the following examples primarily illustrate certain more specific details thereof.

EXAMPLE 1

Winter wheat seeds were germinated in rockwool in GA7 (Magenta, Chicago, Ill.) plastic containers. In each GA7 was placed a 2.5 sq. inch cube of rockwool with 9 wheat seeds and 50 mls. of tap water or a solution of tap water containing 500 ppm GABA. There were 4 replicate GA7's for each treatment. The GA7 containers were kept under continuous light and when the solutions had been used up by the growing plants they were replaced with 50 mls. of water or GABA solution. After 2 weeks growth plants were harvested and oven-dried. The 9 plants from each GA7 were combined and dry weights determined, the results are shown below in Table 1.

TABLE 1

| Treatment | Plant dry wts/GA7-mgs | Average dry wt +/− SD |
|---|---|---|
| Water Control | 253, 229, 320, 252 | 263 +/− 39 |
| GABA-500 ppm | 319, 345, 361, 362 | 347 +/− 20 |

Results show that 500 ppm GABA increased dry weight of wheat seeds on average of 32%. Students t-test showed that the differences were significant at 99% confidence.

EXAMPLE 2

The ability of GABA to promote plant growth when given as a foliar treatment was demonstrated with winter wheat. Plants were grown from seed in 4 inch pots with vermiculite and watered with deionized water. The growing conditions were designed to ensure that plants would be unable to obtain sufficient nutrients for growth through the roots. After 2 weeks growth control plants (4 pots with 4 plants/pot) were sprayed with deionized water. Another 4 pots of plants were sprayed with a foilar fertilizer (Solu-Spray 20-20-20 @10 lbs./acre, Leffingwell Chemical Company). A third group of plants was sprayed with the fertilizer solution containing 250 ppm GABA. Plants were harvested 9 days after the foilar treatments were given, the combined weight of the four plants from each pot was determined. Results below in Table 2 show the average fresh weight +/− standard deviation of the 4 pots from each treatment:

TABLE 2

| Treatment | Mean Fresh Wt. (g) +/− SD | % Change from Cont. |
|---|---|---|
| Control | 2.26 +/− 0.85 | 0 |
| Fertilizer | 2.80 +/− 0.32 | 24 |
| Fertilizer + GABA | 4.70 +/− 0.38 | 108 |

Results show that plants given a foliar application of fertilizer had, on average, 24% greater fresh weight than plants receiving no additional nutrients. However, plants given both the fertilizer and GABA lad more that than twice the fresh weight of control plants.

EXAMPLE 3

Dalkon sprouting radish (Park Seeds, Greensboro, N.C.) were grown in plastic sprouters (Park Seeds). Seedlings were germinated in 10"×20" plastic trays on moist paper towels and transferred to sprouters (200 seedlings/sprouter) when they were two days old. The sprouters contained tap water or GABA, 94.5% fermentation grade succinic acid (FSA), and mixtures of GABA and FSA. After 5 days, seedling root lengths were measured. Each of the treatment results below shown in Table 3 consisted of two replicate sprouters each containing 100 radish sprouts:

TABLE 3

| Treatment | Average Root Length − mm |
|---|---|
| control | 6.7 |
| FSA 50 ppm | 14.0 |
| GABA 50 ppm | 13.4 |
| FSA 25 ppm + GABA 25 ppm | 14.5 |
| FSA 40 ppm + GABA 10 ppm | 14.6 |

Results show that both FSA and GABA alone more than doubled the length of seedling roots. The greatest stimulation of root growth was with mixtures of GABA and FSA, the most effective treatment was with mixtures containing more than 50% succinic acid.

EXAMPLE 4

Duckweed (*Lemna minor L.*) was grown following the general procedure described in U.S. Pat. No. 4,813,997 (Kinnersley, et al.) except that the culture media was Solu-Spray 20-20-20 fertilizer dissolved in tap water at 1 g/L and pH adjusted to 5.5. Equimolar amounts of GABA, synthetic succinic acid (SA) (Sigma Chemical), and mixtures of GABA and succinic acid were added to the fertilizer solution. The effects of the different mixtures on growth of Duckweed was determined after a growing period of 21 days. Each datum below in Table 4 shows the average dry weight +/− SD of 9 replicate cultures for each treatment.

TABLE 4

| Treatments | Average Dry Weight +/− SD | % Change from Control |
|---|---|---|
| Control | 10.2 +/− 4.7 | 0 |
| GABA 5 mM | 18.6 +/− 3.6 | 82 |
| GABA 10 mM | 21.8 +/− 5.2 | 114 |
| GABA 15 mM | 24.8 +/− 5.2 | 143 |
| SA 5 mM | 17.6 +/− 3.5 | 72 |
| SA 10 mM | 26.1 +/− 4.9 | 155 |
| SA 15 mM | 23.0 +/− 2.8 | 125 |
| GABA 7.5 mM + SA 7.5 mM | 29.2 +/− 3.3 | 186 |
| GABA 5.0 mM + SA 10 mM | 31.1 +/− 3.0 | 205 |

The above results show that both GABA and SA alone stimulated plant growth. However, mixtures of GABA and SA were more effective than either acid alone and the results indicate that mixtures of the two acids give greater growth promotion than either acid alone—regardless of how much acid is added to the media. The results of treatments containing 15.0 mM (millimolar) GABA, 15.0 mM SA, and 5.0 mM GABA+10.0 mM SA were analyzed statistically using the Student's t-test. This showed that the mixture was significantly (t>95%) more active at promoting growth than either acid alone. Since all three treatments contained the same number of molecules (15 mM) this shows a synergistic response between GABA and SA.

EXAMPLE 5

Duckweed was grown in accordance with Example 4 and the growth of the duckweed was monitored by counting the number of leaves (fronds) produced in each culture after 1, 3, 4 and 7 days. On day 1, each of 3 replicate cultures was inoculated with a single 3-frond plant. The number of fronds produced on subsequent days were counted and results are shown in Table 5.

TABLE 5

| SA[a] (ppm) | GABA (ppm) | SISA[b] Day | | | | FSA[c] Day | | | |
| --- | --- | --- | --- | --- | --- | --- | --- | --- | --- |
| | | 1 | 3 | 4 | 7 | 1 | 3 | 4 | 7 |
| — | — | 9 | 24 | 32 | 64 | 9 | 25 | 28 | 62 |
| 1000 | — | 9 | 30 | 44 | 112 | 9 | 30 | 39 | 109 |
| 750 | 250 | 9 | 50 | 66 | 171 | 9 | 38 | 47 | 132 |
| 500 | 500 | 9 | 39 | 53 | 128 | 9 | 32 | 65 | 114 |
| 250 | 750 | 9 | 33 | 46 | 120 | 9 | 31 | 43 | 110 |
| — | 1000 | 9 | 34 | 46 | 112 | 9 | 30 | 41 | 97 |

[a]SA = succinic acid.
[b]SISA = synthetic succinic acid (Sigma).
[c]FSA = fermention-derived succinic acid (Michigan Biotechnology Institute).

The results show that the greatest stimulation of plant growth was found when the amount of succinic acid in the succinic acid: GABA mixtures was greater than 50%. The results also show that mixtures of synthetic succinic acid and GABA were more active at increasing plant growth than comparable mixtures of fermention-derived succinic acid.

EXAMPLE 6

Duckweed was grown as in Example 4 and was treated with synthetic succinic acid (Sigma) alone and in combination with GABA, each in the amounts shown in the column labeled "Treatment" in Table 6a and 6b. In Table 6a, column 2 shows the dry weight of duckweed harvested after 19 days, and column 3 shows the weight change or difference in mg's as compared to the control. Column 4 shows a ratio of the weight of succinic acid divided by the weight change of column 3.

Table 6b is similar to Table 6a, except that in Table 6b the control is 950 ppm SA; column 3 shows the weight change or difference of duckweed for each row as compared to row 1 (SA alone) and column 4 shows a ratio of the weight of GABA divided by column 3, the weight change.

TABLE 6a

| Treatment (wt. SA) | Dry Wt.-mg. Duckweed | Wt. change – mg Compared to Control | Wt SA/ Wt. Change |
| --- | --- | --- | --- |
| Control | 10.2 | — | — |
| 1000 ppm SA (40 mg) | 20.3 | 10.1 | 3.96 |
| 950 ppm SA (38 mg) | 19.8 | 9.6 | 3.96 |

TABLE 6b

| Treatment (wt. SA) | Dry Wt.-mg Duckweed | Wt. change compared to 950 ppm SA alone | Wt. GABA/ dry wt. of Duckweed |
| --- | --- | --- | --- |
| 950 ppm SA (38 mg) | 19.8 | — | — |
| 950 ppm SA + 2 mg GABA | 25.0 | 5.2 | 0.38 |
| 950 mg SA + 1 mg GABA | 24.1 | 4.3 | 0.23 |

Based on the results shown in Tables 6a and 6b, GABA is ten fold more bioactive than synthetic succinic acid and GABA is not promoting growth by acting as a carbon source. That is, when using synthetic succinic acid alone, 3.96 mg of synthetic succinic acid is required to cause 1.0 mg wt. change, whereas between 0.23 mg and 0.38 mg of GABA in a synthetic succinic acid solution causes 1.0 mg of weight change as compared to succinic acid alone.

Thus, the present invention provides a method for increasing plant growth and productivity by treating the roots, stems and/or foliage of the plant with an effective amount of GABA. Further, the present invention provides a process for increasing the rate of root formation in a plant.

Having thus described various preferred embodiments of the invention and several of its benefits and advantages, it will be understood by those of ordinary skill that the foregoing description is merely for the purpose of illustration in that numerous substitutions, rearrangements and modifications may be made in the invention without departing from the scope and spirit of the appended claims. For example, the processes described herein may be implemented through the application of solids, as well as liquids, to growing plants; it being understood that such solids are eventually dissolved in water and taken up by the plants.

What is claimed is:

1. A process for increasing growth of a plant comprising treating the plant with γ-aminobutyric acid and succinic acid.

2. The process of claim 1 wherein the succinic acid is selected from the group consisting of synthetic succinic acid and fermention-derived succinic acid.

3. The process of claim 1 further comprising treating the plant with synthetic succinic acid.

4. The process of claim 2 wherein the plant is treated with a solution having in the range of from about 2.5% to about 50% γ-aminobutyric acid and in the range of from about 97.5%% to about 50% succinic acid with a suitable carrier medium.

5. The process of claim 1 wherein the plant is treated with a solution having in the range of from about 1 ppm to about 5000 ppm γ-aminobutyric acid in a suitable carrier medium.

6. The process of claim 1 wherein the plant is grown hydroponically.

7. The process of claim 1 wherein said treating comprises treating the foliage of the plant with γ-aminobutyric acid and succinic acid.

8. The process of claim 7 wherein the succinic acid is selected from the group consisting of synthetic succinic acid and fermention-derived succinic acid.

9. The process of claim 8 wherein the plant is treated with a solution having in the range of from about 2.5% to about 50% γ-aminobutyric acid and in the range of from about 97.5% to about 50% succinic acid with a suitable carrier medium.

10. The process of claim 7 wherein the plant is treated with a solution having in the range of from about 1 ppm to about 5000 ppm γ-aminobutyric acid in a suitable carrier medium.

11. The process of claim 7 wherein the plant is grown hydroponically.

12. A process for increasing the rate of root formation in a plant, the process comprising treating the plant with γ-aminobutyric acid and succinic acid.

13. The process of claim 12 wherein the succinic acid is selected from the group consisting of synthetic succinic acid and fermention-derived succinic acid.

14. The process of claim 13 wherein the plant is treated with a solution having in the range of from about 2.5% to about 50% γ-aminobutyric acid and in the range of from about 97.5% to about 50% succinic acid with a suitable carrier medium.

15. The process of claim 12 wherein the plant is treated with a solution having in the range of from about 1 ppm to about 5000 ppm γ-aminobutyric acid in a suitable carrier medium.

16. The process of claim 12 wherein the plant is grown hydroponically.

17. A process for increasing the rate of growth of a seed and seedling comprising applying γ-aminobutyric acid and succinic acid in a suitable carrier to a seed under germination conditions.

18. A process of claim 17 wherein the succinic acid is selected from the group consisting of synthetic succinic acid and fermention-derived succinic acid.

19. The process of claim 17 wherein the composition is a solution having in the range of from about 2.5% to about 50% γ-aminobutyric acid and in the range of from about 97.5% to about 50% succinic acid with a suitable carrier medium.

* * * * *